United States Patent [19]

Sigler et al.

[11] Patent Number: 5,439,798
[45] Date of Patent: Aug. 8, 1995

[54] MALEIMIDE ADDUCT CONJUGATES OF PROCAINAMIDE AND NAPA

[75] Inventors: Gerald F. Sigler; Charles F. Walter, both of Carmel; Charles E. Durant, Indianapolis; Todd Glancy, Fairmount, all of Ind.; Frank E. Klein, Elkton, Md.; Allan R. Dorn, Carmel, Ind.

[73] Assignee: Boehringer Mannheim Corporation, Indianapolis, Ind.

[21] Appl. No.: 169,851

[22] Filed: Dec. 17, 1993

[51] Int. Cl.⁶ .............. G01N 33/542; C07K 16/44; C12N 9/96; C07D 207/448
[52] U.S. Cl. ..................... 435/7.7; 435/188; 436/544; 436/545; 436/822; 530/388.9; 530/389.8; 530/404; 548/546
[58] Field of Search .............. 435/188, 7.7; 530/389.8, 404, 388.9; 548/546; 436/544, 545, 822

[56] References Cited

U.S. PATENT DOCUMENTS

| | | | |
|---|---|---|---|
| 4,235,969 | 11/1980 | Singh et al. | 435/188 |
| 4,673,763 | 6/1987 | Buckler et al. | 564/155 |
| 4,708,929 | 11/1987 | Henderson | 435/188 |

FOREIGN PATENT DOCUMENTS

199042 10/1986 European Pat. Off.

OTHER PUBLICATIONS

M. Brinkley, Bioconjugate Chem., vol. 3, pp. 2–13 (1992).
P. Mojaverian et al., J. Pharm. Sci., vol. 69, pp. 721–724 (1980).
L. Adams et al., Int. J. Immunopharmacol., vol. 15, No. 8, pp. 887–897 (1993).
A. Russel et al., Clin. Exp. Immunol., vol. 3, pp. 901–909 (1968).

Primary Examiner—Mary E. Ceperley
Attorney, Agent, or Firm—Marilyn L. Amick; Max J. Kenemore; D. Michael Young

[57] ABSTRACT

Novel derivatives of procainamide and N-acetyl-procainamide (NAPA) are disclosed having the following formula:

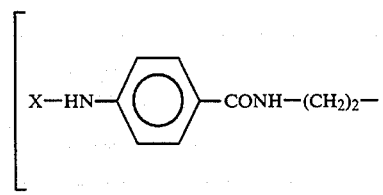

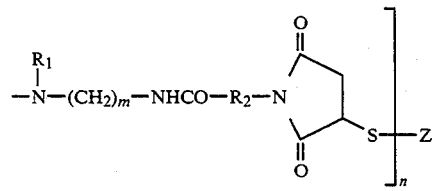

wherein:
X=hydrogen or acetyl;
$R_1$=an alkyl group having 1 to 3 carbon atoms;
m=an integer from 2 to 10;
$R_2$=an alkyl, cycloalkyl or aryl group having 2 to 10 carbon atoms;
Z=a poly(amino acid); and
n=1 to p where p=MW of Z/1000.

The derivatives include maleimide conjugates of proteins or poly(amino acids), enzymes, enzyme donor polypeptides and labeling substances. Novel activated hapten intermediates useful in the preparation of the conjugates and methods for synthesis of the hapten intermediates and derivatives are also disclosed.

18 Claims, 4 Drawing Sheets

MALEIMIDE ADDUCT CONJUGATES OF PROCAINAMIDE AND NAPA

BACKGROUND

The present invention relates to novel derivatives of procainamide and N-acetylprocainamide (NAPA). The derivatives include immunogens used to stimulate antibody production and polypeptide conjugates useful in immunoassays for detecting procainamide and NAPA. Also provided are hapten intermediates in the synthesis of the immunogens and polypeptide conjugates.

The cardiac depressant drugs procainamide and N-acetylprocainamide are used clinically to treat or prevent cardiac arrhythmia. N-acetylprocainamide (abbreviated as NAPA and also known as acecainide) is the major metabolite of procainamide in man. The concentration of this metabolite in the plasma of patients receiving procainamide often exceeds the concentration of the parent drug itself. Metabolism is by in vivo acetylation, and much genetic-based variation has been observed in the rate at which individual patients transform the drug to its metabolite. This phenomenon is of importance in the clinical use of the drugs because of the lower incidence of side effects associated with NAPA. Both the therapeutic usefulness and the toxicity of the drugs are better correlated with their blood levels than with their dosages. The relationship between the amount of drug administered and the blood levels is quite variable. It is influenced by completeness of absorption, distribution characteristics and rates of metabolism and excretion.

Because of these considerations, numerous analytical methods have been developed to determine blood levels of these drugs, including high pressure liquid chromatography (HPLC), quantitative thin layer chromatography (TLC), and immunoassay, including enzyme immunoassay and immunoassay using fluorescence techniques. Competitive binding immunoassays have proved to be particularly advantageous. In such assays, an analyte in a biological sample competes with a labeled reagent, or analyte analog, or tracer, for a limited number of receptor binding sites on antibodies specific for the analyte and analyte analog. Enzymes, fluorescent molecules, and radioactive compounds are common labeling substances used as tracers. The concentration of analyte in the sample determines the amount of analyte analog which binds to the antibody. The amount of analyte analog that will bind is inversely proportional to the concentration of analyte in the sample, because the analyte and the analyte analog each bind to the antibody in proportion to their respective concentrations. The amount of free or bound analyte analog can then be determined by methods appropriate to the particular label being used.

One type of competitive binding immunoassay is based upon the reassociation of polypeptide fragments to form active enzymes as a step of generating a detectable signal utilized to determine the amount of analyte present in a sample. This type of assay, known as cloned enzyme donor immunoassay (CEDIA), is described in U.S. Pat. No. 4,708,929, the content of which is herein incorporated by reference. In particular, a $\beta$-galactosidase enzyme donor polypeptide combines with a $\beta$-galactosidase enzyme acceptor polypeptide to form active $\beta$-galactosidase enzyme conjugating a hapten, or a small analyte or an analyte analogue, to the enzyme donor polypeptide at certain sites does not affect the ability to form $\beta$-galactosidase by a complementation reaction and hence does not affect the rate of $\beta$-galactosidase activity when in the presence of a substrate for $\beta$-galactosidase. However, when the enzyme donor-hapten conjugate is bound by anti-analyte antibody, the complementation rate is impeded, and thereby the enzyme-catalyzed reaction rate during the initial phase of the reaction is reduced. This reduction in enzyme-catalyzed reaction rate can be monitored and has been used to quantitate the determination of a plurality of analytes on the principle of competitive inhibition where enzyme donor-analyte conjugate present in a reaction mixture and analyte present in the sample compete for anti-analyte antibody prior to the addition of enzyme acceptor. The complementation rate of $\beta$-galactosidase formation, and hence enzyme catalyzed reaction rate, is increased as the amount of analyte present in the sample is increased.

In accepted clinical practice, procainamide and NAPA are analyzed separately. Therefore immunoassays for NAPA and procainamide require antibodies with a high degree of specificity for either the metabolite or the drug. Since the metabolite and drug differ only by the presence or absence of an acetyl function, the generation of specific antibodies is a particularly challenging problem. Surprisingly, however, the immunogens of the present invention have been found to be especially useful for this purpose.

The preparation of antibodies to procainamide and NAPA for use in immunoassays to determine the drugs has been accomplished in the prior art by essentially three different approaches. One approach has been to couple procainamide through the benzene ring amino group by diazotization and subsequent condensation to an albumin carrier [A. S. Russel et al., *Clin. Exp. Immunol.* 3:901 (1968) and Mojaverian et al., *J. Pharm. Sci.* 69:721 (1980)]. The resulting antibodies show a high degree of cross-reactivity with NAPA, however, and are therefore unsuitable for use in immunoassays specific for one or the other drug.

The second approach involves coupling of the drugs at the opposite end of their structures, at the N-diethylamino group, by modification of one of the ethyl substituents for subsequent coupling to an antigenic carrier. As a result, antibodies are raised against an immunogen in which a major functional group of the drugs has been modified in order to couple them to the carrier. An example of this approach is described in U.S. Pat. No. 4,235,969 issued to Singh et al., in which one of the N-alkyl groups is replaced with a nonoxocarbonyl-alkyl substituent. The nonoxocarbonyl functionality, a linking group containing a carbonyl or imino function, is employed for conjugation to antigens and enzymes. Similarly, European Appl. No. 86103161.5 (Heiman et al.) discloses antigenic conjugates and enzyme conjugates of procainamide analogs modified at the terminal diethylamino group. A specific linking group is attached to a poly(amino acid) or a fluorescein tracer.

In a third approach, Buckler et al., U.S. Pat. No. 4,673,763, describe derivatives of procainamide or NAPA coupled at the $\alpha$-position of the amide side chain to an immunogenic carrier material or to a label.

The conjugates described in the Singh, Heiman and Buckler publications all utilize amide bond condensation chemistry with amino- or carboxyl-functionalized haptens. The present invention, however, differs from the linker chemistry of the prior art. In the conjugates of the present invention, maleimide modified haptens are reacted with sulfhydryl groups on carrier proteins, enzymes or enzyme donor polypeptides to give thioether linked hapten conjugates. Maleimide/sulfhydryl chemistry [M. Brinkley, *Bioconjugate Chem.* 3:5 (1992)] is more easily controlled than amide bond condensation, thus allowing the preparation of immunogens and enzyme or enzyme donor conjugates with defined, targeted degrees of substitution, a feature which is very important to the functional efficacy of the conjugates.

Two other metabolites of procainamide and NAPA that have recently been identified are desethyl procainamide (PADE) and desethyl N-acetylprocainamide (NAPADE) [Ruo et al., *Ther. Drug Monitoring,* vol. 3:231 (1981) and Ruo et al., *J. Pharm. Exp. Ther.,* vol. 216:357 (1981)]. Since the immunogens of the present invention are hapten derivatives of the desethyl compounds, it would be expected that antibodies derived from such immunogens would show a high degree of cross-reactivity with PADE and NAPADE and would therefore be unsuitable for use in the assay of procainamide and NAPA. Quite surprisingly, however, the antibodies of the present invention show a low cross-reactivity, less than about 10 percent, with PADE and NAPADE. Such low cross-reactivity with desethyl metabolites is highly desirable for accurate clinical analysis, and the prior art has failed to address the problem of cross-reactivity with these metabolites.

SUMMARY OF THE INVENTION

The present invention provides novel activated hapten derivatives of the following formula:

X—HN—〈phenyl〉—CONH—(CH$_2$)$_2$—

—N(R$_1$)—(CH$_2$)$_m$—NHCO—R$_2$—N(maleimide)

wherein:
X = hydrogen or acetyl;
R$_1$ = an alkyl group having 1 to 3 carbon atoms, preferably 2 carbon atoms;
m = an integer from 2 to 10, preferably 2; and
R$_2$ = an alkyl, cycloalkyl or aryl group having 2 to 10 carbon atoms, preferably (CH$_2$)$_2$.

The present invention further provides novel hapten conjugates of the formula:

[ X—HN—〈phenyl〉—CONH—(CH$_2$)$_2$—

—N(R$_1$)—(CH$_2$)$_m$—NHCO—R$_2$—N(succinimide-S—Z) ]$_n$ wherein:
X = hydrogen or acetyl;
R$_1$ = an alkyl group having 1 to 3 carbon atoms, preferably 2 carbon atoms;
m = an integer from 2 to 10, preferably 2;
R$_2$ = an alkyl, cycloalkyl or aryl group having 2 to 10 carbon atoms, preferably (CH$_2$)$_2$;
Z = an immunogenic poly(amino acid) an enzyme donor polypeptide or a labeling group; and
n = 1 to p where p = MW of Z/1000.

The present invention uniquely provides reagents for use in procainamide and NAPA immunoassays involving the coupling to or derivatization of the maleimide modified activated hapten precursor compound via sulfhydryl groups on a poly(amino acid). The immunogens of the present invention, which comprise the haptenic drug covalently linked via its maleimide moiety and a sulfhydryl bridge to an immunogenic carrier material, are used to stimulate the production of antibodies to the respective drugs. Antibodies prepared using the novel immunogens of the invention have been found to show surprisingly low cross-reactivity with the desethyl metabolites of procainamide and NAPA.

In another aspect, the present invention provides immunoassay methods and reagents for the determination of NAPA and procainamide using the novel antibodies. The present invention also provides novel hapten-enzyme or hapten-enzyme donor conjugates for particularly preferred embodiments of the assay methods.

BRIEF DESCRIPTION OF THE DRAWINGS

The present invention will be better understood by reference to the following detailed description of the invention when considered in combination with the drawings that form part of the specification, wherein.

DESCRIPTION OF PREFERRED EMBODIMENTS

The present invention, in all of its interrelated embodiments, is focused on the preparation of maleimide derivatives of NAPA and procainamide which can then be used to form immunogens by coupling the derivatives to conventional antigenic poly(amino acid) or other carrier materials and subsequently used to obtain antibodies, or the derivatives can be used to form enzyme, enzyme donor or labeled conjugates which are useful as detection reagents in immunoassays for the drugs.

The chemical structures of NAPA and procainamide are represented by the formula:

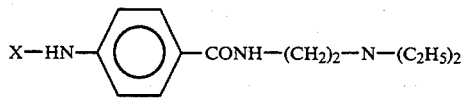

wherein X is hydrogen for procainamide and acetyl for NAPA.

Figure 1:
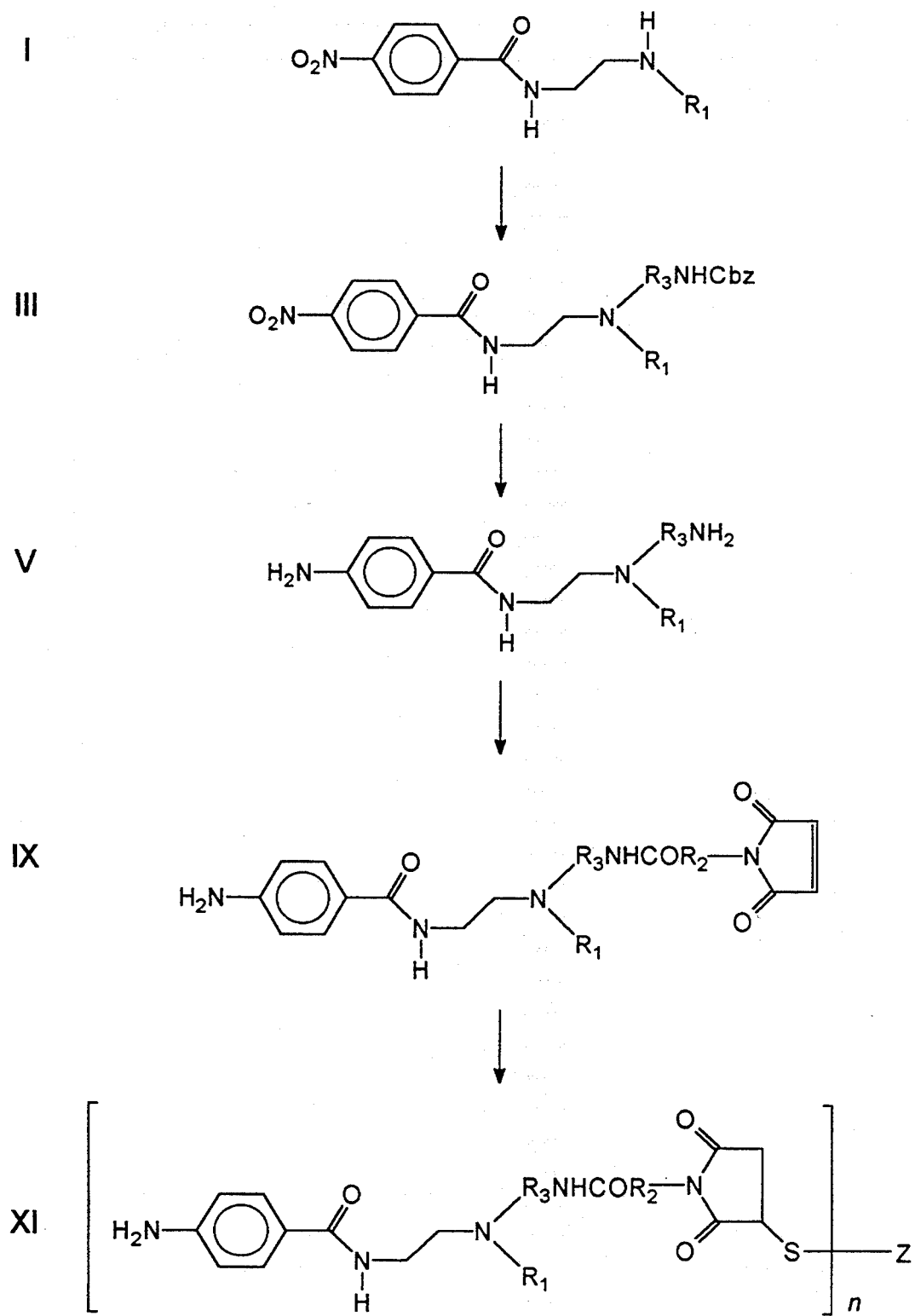
FIGS. 1 and 2 illustrate particular synthetic schemes for preparing maleimide derivatives of NAPA and procainamide and for preparing particularly useful precursor compounds for use in such derivatizations of the drugs.

In a preferred embodiment of the present invention, maleimide haptens of the drugs and immunogen conjugates are synthesized according to the scheme shown in FIG. 1. Compound I is synthesized according to the method of, e.g., Ruo et al., *Ther. Drug Monitoring* 3:231 (1981), the content of which is herein incorporated by reference. Compound III is generated from I by alkylation with an N-carbobenzoxy bromoalkylamine. This is reduced to V by catalytic hydrogenation. The reactive intermediate IX is obtained by acylation of V with maleimido-alkanoic acid N-hydroxysuccinimide ester, which is then coupled through the free sulfhydryl groups of a poly(amino acid) to generate compound XI.

Figure 2:
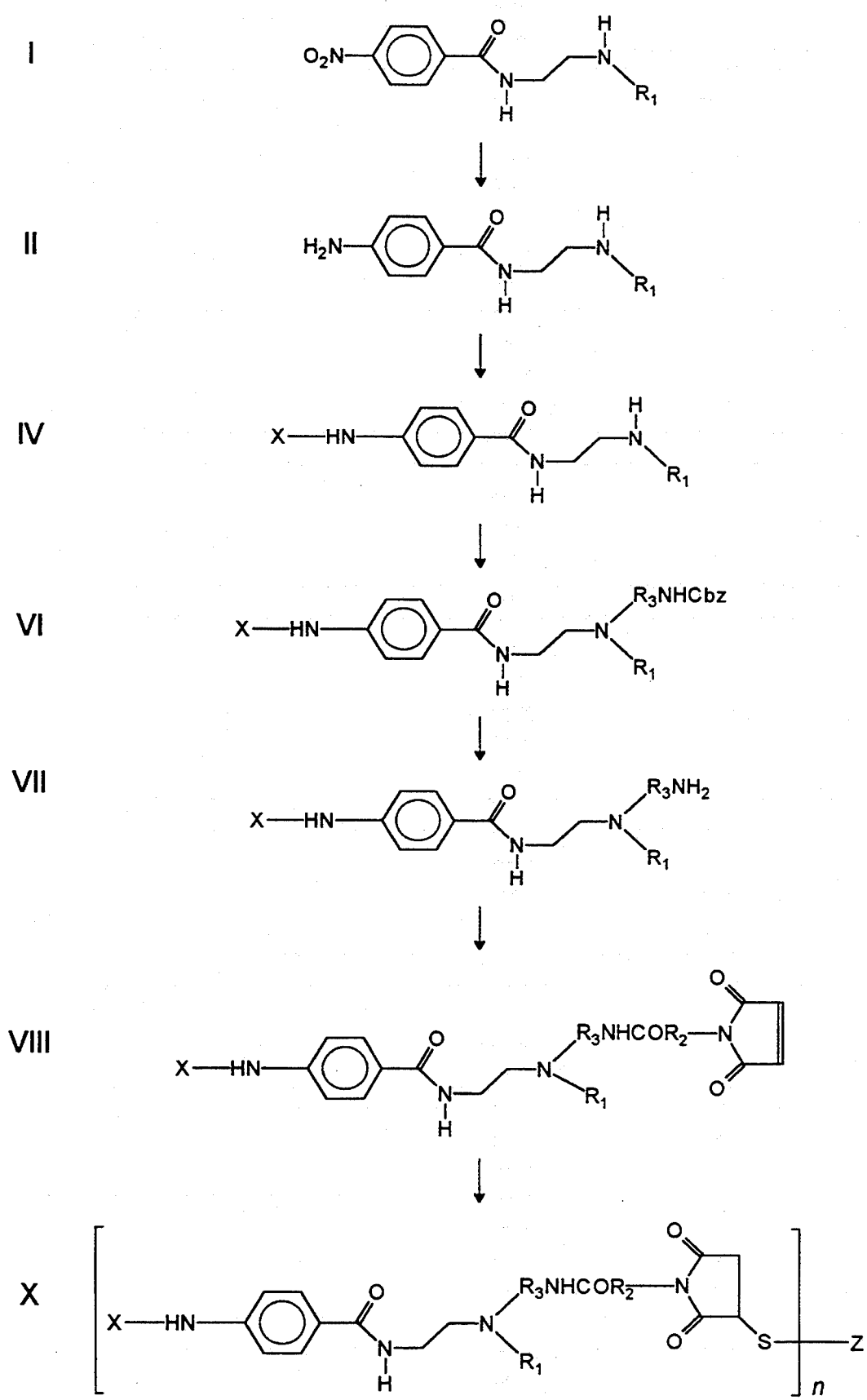

In another preferred embodiment of the invention, maleimide derivatives of the drugs and immunogen conjugates are synthesized according to the scheme shown in FIG. 2. Catalytic hydrogenation of compound I yields II. Selective acetylation of compound II with acetic anhydride gives compound IV. This compound is then alkylated with an N-carbobenzoxy bromoalkylamine to produce VI. Compound VI is hydrogenated to remove the carbobenzoxy (Cbz) group and generate free amine VII. Compound VII is acylated with maleimido-alkanoic acid N-hydroxysuccinimide ester to give VIII. Finally, VIII is coupled to the free sulfhydryl groups of a poly(amino acid) to give product X.

Examples of suitable $R_2$ linking groups include ethyl, propyl, butyl, cyclopentyl, cyclohexyl, methylcyclohexyl, phenyl, benzyl, and substituted derivatives thereof.

In preparing the immunogens of the invention, a thiol-containing carrier protein or other substance having immunogenic properties is coupled to the maleimide hapten. Although thiolated keyhole limpet hemocyanin (KLH) is an especially preferred antigenic poly(amino acid), or carrier protein, it should be understood that various protein carriers may be employed, including albumins, serum proteins, e.g., globulins, ocular lens proteins, lipoproteins and the like. Illustrative protein carriers include bovine serum albumin, egg ovalbumin, bovine gammaglobulin, thyroxine binding globulin, etc. Alternatively, synthetic poly(amino acids) having a sufficient number of available sulfhydryl groups such as cysteine may be employed, as may other synthetic or natural polymeric materials bearing reactive functional groups. In particular, carbohydrates, yeasts, or polysaccharides may be conjugated to the hapten to produce an immunogen.

Enzyme donor conjugates are prepared by coupling the donor polypeptide to the maleimide hapten. The enzyme donor peptides suitable for maleimide-hapten conjugation are those which contain cysteine groups. The hapten to enzyme donor conjugation ratio should be at least a 10-fold excess of hapten.

Conjugates of the activated hapten and a labeling group such as an enzyme, a substance having fluorescent properties, or a radioactive label may also be prepared and used as reagents in immunoassays. As with the immunogen and enzyme donor conjugates, the label employed must have available thiol-containing groups to be suitable for use in the present invention. The thiol groups may be naturally occurring or they may be artificially introduced using a thiolating agent such as N-succinimidyl-3-(acetylthio) propionate (SATP).

In order to generate antibodies, the immunogen is conveniently prepared for injection into a host animal by rehydrating lyophilized immunogen to form a solution or suspension of the immunogen. The immunogen solution is then combined with an adjuvant such as Freund's. The immunogen may be administered in a variety of sites, at several doses, one or more times, over many weeks.

Preparation of polyclonal antibodies using the immunogen may follow any of the conventional techniques known to those skilled in the art. Commonly, a host animal such as a rabbit, goat, mouse, guinea pig, or horse is injected with the immunogen mixture. Further injections are made, with serum being assessed for antibody titer until it is determined that optimal titer has been reached. The host animal is then bled to yield a suitable volume of specific antiserum. Where desirable, purification steps may be taken to remove undesired material such as nonspecific antibodies before the antiserum is considered suitable for use in performing assays.

Monoclonal antibodies may be obtained by hybridizing mouse lymphocytes, immunized as described above, and myeloma cells using a polyethylene glycol method such as the technique described in *Methods in Enzymology*, vol. 73 (Part B), pages 3–46 (1981).

EXAMPLE 1

Synthesis of p-amino-N-[(2-ethylamino)ethyl]-N'-[2-(3-maleimido-propionamido)ethyl]-benzamide Referring to FIG. 1, in which $R_1=CH_2CH_3$, $R_2=(CH_2)_2$, and $R_3=(CH_2)_2$, p-amino-N-[(2-ethylamino)ethyl]-N'-[2-(3-maleimido-propionamido)ethyl]-benzamide (IX) was synthesized according to the following scheme:

p-Nitro-N-[2-(ethylamino)ethyl]benzamide (I) was first synthesized from N-ethyl-ethylenediamine and p-nitrobenzoyl chloride using the method of Ruo et al., ibid. Of this intermediate, 233 mg was dissolved in 2.5 ml of N,N-dimethylformamide (DMF) and treated with 266 mg of N-carbobenzoxy-2-bromoethylamine [E. Katchalski and D. B. Ishai, *J. Org. Chem.* 15:1067 (1950)] in the presence of 282 mg of anhydrous potassium carbonate. After stirring 20 hr. at room temperature, the suspension was rotary evaporated to a volume of 1 ml and reacted another 20 hr. The reaction mixture was then filtered and rotary evaporated to an oil. The crude product was dissolved in chloroform, 25ml, and washed sequentially in a separatory funnel with 10 ml portions of water, 1M sodium bicarbonate and saturated sodium chloride solution. The chloroform solution was dried over sodium sulfate, filtered and evaporated to an oil. The product was purified from unreacted starting materials by silica gel chromatography with chloroform/methanol, 95:5 v/v, as eluent to give 167 mg of p-nitro-N-[(2-ethylamino)ethyl]-N'-[2-carbobenzoxy-aminoethyl]-benzamide (III). The latter intermediate was dissolved in a mixture of 10 ml ethanol and 0.8 ml of 1 N hydrochloric acid. The mixture was hydrogenated in a Parr reactor at 50 psi hydrogen in the presence of 121 mg of 10% palladium/charcoal catalyst. After shaking for 2 hr. at room temperature, the hydrogenation was stopped and the suspension was filtered through a bed of celite to remove catalyst. The ethanol filtrate was rotary evaporated to a film. The product was precipitated from ethanol/diethyl ether to give 75 mg of p-amino-N-[(2-ethylamino)ethyl]-N'-[2-aminoethyl]-benzamide dihydrochloride (V). This amine intermediate, 39 mg, was dissolved in 1.4 ml of DMF. Triethylamine, 0.034 ml, was added followed by 32 mg of 3-maleimido-propionic acid N-hydroxysuccinimide ester. The resultant mixture was stirred at room temperature for 18 hr. The DMF solution of maleimide adduct was loaded on a preparative HPLC column (Vydac, 2.2×25 cm C18) equilibrated with 0.1% aqueous trifluoroacetic acid (TFA). The column was eluted at 4ml/min with a 20 min linear gradient of 0–15 % acetonitrile containing 0.1% TFA, while monitoring at 260 and 280 nm. The major peak was collected and lyophilized to yield 29.7 mg of maleimide adduct based upon UV extinction at the maximum of 279 nm. 1H-NMR of the product confirmed the target structure IX [i.e., maleimide resonance at 6.8 ppm (singlet), p-aminobenzamide resonances at 7.2 and 7.8 ppm (doublets), alkyl resonances at 1.4 ppm ($CH_3$ triplet), 2.5 ppm ($CH_2$—CO triplet), and 3.3–4.0 ppm ($CH_2$—N overlapping multiplets)].

EXAMPLE 2

Synthesis of p-acetamido-N-[(2-ethylamino)ethyl]-N'-[2-(maleimido-propionamido)ethyl]-benzamide Referring to FIG. 2, in which X=$CH_3CO$, $R_1$=$CH_2CH_3$, $R_2$=$(CH_2)_2$ and $R_3$=$(CH_2)_2$, p-acetamido-N-[(2-ethylamino)ethyl]-N'-[2-(maleimido-propionamido)ethyl]benzamide (VIII) was synthesized according to the following scheme:

p-Acetamido-N-[(2-ethylamino)ethyl]-benzamide or desethyl-NAPA (IV) was first synthesized from p-nitro-N[(ethylamino)ethyl]benzamide (I) by reduction to desethyl procainamide followed by acetylation using the methods of Ruo et al (ibid.). The desethyl NAPA, 152 mg, was dissolved in 2 ml of DMF and treated with 160 mg of N-carbobenzoxy-2-bromoethylamine and 166 mg anhydrous potassium carbonate by stirring at room temperature for 53 hr. An additional 169 mg of N-carbobenzoxy-2-bromoethylamine in 2 ml DMF was then added and the mixture was stirred for 21 hr. Finally, a third portion of N-carbobenzoxy-2-bromoethylamine was added in 2 ml DMF and the reaction was continued for 3 more days, at which time TLC indicated nearly complete reaction. The reaction mixture was then filtered and rotary evaporated to an oil. The oil was redissolved in chloroform, 20 ml, and washed sequentially in a separatory funnel with 10 ml portions of 1M sodium bicarbonate and saturated sodium chloride solution. The chloroform solution was dried over anhydrous sodium sulfate, filtered and rotary evaporated to give crude product. Purification was accomplished by silica gel chromatography with chloroform/methanol eluents (95:5 and 90:10 v/v) to give 100 mg of p-acetamido-N-[(2-ethylamino)ethyl]-N'-[2-carbobenzoxy-aminoethyl]-benzamide (VI) as an oil. The latter intermediate was dissolved in 20 ml of methanol and hydrogenated in a Parr reactor at 38 psi hydrogen for 1.5 hr. in the presence of 100 mg of 10% palladium/charcoal catalyst. The catalyst was filtered off and the filtrate was diluted with 0.8 ml of 1 N hydrochloric acid. Rotary evaporation gave a film which was redissolved in ethanol and precipitated with diethyl ether to give 54 mg of solid p-acetamido-N-[(2-ethylamino)ethyl]-N'-(2-aminoethyl)-benzamide dihydrochloride (VII). This amine intermediate, 44 mg, was dissolved in 1.4 ml of DMF. Triethylamine, 0.034 ml was added followed by 34 mg of maleimido-propionic acid N-hydroxysuccinimide ester. The reaction mixture was stirred at room temperature for 6 hr. Purification was accomplished by preparative HPLC as in Example 1 above with the exception that a 5–20% gradient over 15 min. was employed. The major peak from the HPLC was lyophilized to give 29 mg based upon UV extinction at the maximum of 268 nm. 1H-NMR confirmed the target structure (VIII) [i.e., maleimide resonance at 6.8 ppm (singlet), p-acetamidobenzamide resonances at 7.55 and 7.7 ppm (doublets), acetyl methyl resonance at 2.2 ppm, and alkyl resonances at 1.35 ppm (triplet), 2.4 ppm (triplet) and 3.3–4.0 ppm (overlapping multiplets)].

EXAMPLE 3

Preparation of Immunogens

Procainamide and NAPA immunogens were prepared by coupling the activated maleimide haptens, Compounds VIII and IX, respectively, with thiolated keyhole limpet hemocyanin (KLH). For the maleimide modified haptens to be coupled to the KLH, sufficient sulfhydryl groups must be present on the KLH. This was accomplished through the use of the thiolating agent N-succinimidyl-3-(acetylthio) propionate (SATP).

Thiolation of KLH

KLH was solubilized by dissolving 100 mg in 20 ml of phosphate buffered saline and then mildly sonicating and stirring at room temperature. A 300 molar excess of SATP was used to thiolate the KLH for coupling to Compounds VIII and IX. In 1 ml dimethylformamide (DMF), 73.5 mg of SATP was dissolved. The KLH was slowly added to the SATP while stirring at room temperature. The reaction mixture was incubated for 1 hour at room temperature and then a 1/10 volume of 1M lysine was added (final concentration 100 mM) and incubation was continued for an additional 15 min. The KLH-SATP was dialyzed against 50 mM phosphate, pH 7.4 in 50,000 molecular weight cutoff Spectropore ™ (Spectrum Medical) dialysis tubing overnight (4L×4 changes). Thiol incorporation was determined spectrophotometrically by reaction with 5,5'-dithio-bis-2-nitrobenzoic acid (DTNB) and was found to be 33 moles per mole of KLH.

Conjugation of Compound VIII and Compound IX to KLH

One quarter of the KLH-SATP was used for compound VIII coupling and ¼ for compound IX. The remainder was saved for later use. To ½ of the dialyzed KLH-SATP, a 1/10 volume of 1M hydroxylamine (final concentration 100 mM) was added to deprotect the sulfhydryl, and the reaction was incubated for 1 hour at room temperature. The deprotected material was divided in half and placed into two test tubes. Twenty mg of compound VIII and 20 mg of compound IX were dissolved in 1.67 ml DMF each, and one was added to each of the two deprotected KLH-SATP samples in test tubes, i.e., one tube contained compound VIII and KLH-SATP and the other tube contained compound IX and KLH-SATP. The reaction mixtures were incubated for 4 hours at room temperature while stirring slowly. The mixtures were transferred to 50,000 molecular weight cutoff Spectropore tubing and dialyzed against distilled water, 4 L×3 times. UV analysis indicated the thiols on the KLH were saturated with hapten. Samples were aliquoted into vials (1 mg/vial), frozen at −70° C., and lyophilized. The lyophilized samples were then stored at −20° C. for later use as immunogens.

EXAMPLE 4

Conjugation of compound VIII (or compound IX) to a peptide fragment of β-galactosidase The peptide fragment of β-galactosidase that was used in this example (ED28) consists of β-galactosidase amino acids 1–46 with cysteines at positions 1 and 46, as described in Manning et al., European application no. 90308937.3. To remove reducing reagent that is used in the storage buffer for this compound, 3.3 mg of ED28 was desalted on a NAP5 TM (Pharmacia) desalting column into 1 ml 50 mM sodium phosphate, pH 7.0. One mg, or 1 μmol, of this material was used for the coupling reaction. One μmol of compound VIII was dissolved in 100 μl of dimethylformamide (DMF). To 1 μmole of compound VIII, 1 mg of desalted ED28 was added dropwise while stirring slowly. This was incubated for 1 hr at room temperature. To prepare the sample for HPLC purification, the conjugate mixture was desalted on a NAP5 column equilibrated with water, 0.1% TFA to remove excess hapten. The conjugate was purified on a C4 semi-preparative HPLC column (Vydac) at 4 ml/min using a 25–40% gradient over 15 minutes with solvent A being water/0.1% TFA and B being acetonitrile/0.1% TFA, and the major peak was collected and stored at −20° C. In this procedure, two moles of compound VIII were coupled to each mole of ED28 through the two thiols on the peptide. The same procedure was followed for compound IX-ED28 coupling.

EXAMPLE 5

Preparation of Antibodies

Immunization of Host

Preparation of the immunogen and immunization of the host are accomplished using techniques which will be known to those skilled in the art. The immunogen can be prepared for injection into the host animal by rehydrating lyophilized immunogen in phosphate buffered saline (PBS). The antigen solution is then combined with equal amounts by volume of Freund's adjuvant to form an emulsion. The first immunization can be completed with Complete Freund's Adjuvant and all subsequent immunizations with Incomplete Freund's Adjuvant. The immunogen may be administered in a variety of sites, at several doses, one or more times, over many weeks.

Selection of Antibody

In this example, supernatants were selected from 96-well culture plates using a CEDIA homogeneous assay. As previously described, the CEDIA assay utilizes two genetically engineered, enzymatically inactive fragments of β-galactosidase. The smaller polypeptide, designated the enzyme donor, can recombine spontaneously with the larger fragment, the enzyme acceptor, to form active β-galactosidase, in a process called complementation. When a specific antibody to the ligand attaches to the enzyme donor conjugate, complementation is inhibited. The addition of free ligand to this system will modulate the inhibition of complementation. This assay principle was used to screen fusion products in a 96-well format.

A primary screening of the fusion products was first performed to evaluate the ability of the antibodies to bind to enzyme donor conjugate prepared in Example 4 and inhibit complementation. The number of inhibition-positive clones were then narrowed further by performing a secondary screening assay to determine whether the free drug would modulate or compete with the enzyme donor conjugate for the antibody. The modulation assay also identified specific clones when screened against cross reacting analytes. The clones which modulated with the specific analytes of choice were then grown for further study. The culture supernatant containing the monoclonal antibody was collected and evaluated on the HITACHI 717 autoanalyzer (Boehringer Mannheim Corp., Indianapolis, Ind.) as described in Example 6 below.

EXAMPLE 6

Assays for Procainamide and NAPA

CEDIA assays for procainamide and NAPA were performed using the enzyme donor conjugates prepared in Example 4 and the antibodies produced according to Example 5. The following reagents were prepared:

| Donor reagent: | |
| --- | --- |
| Enzyme donor conjugate | 0.5 nM |
| Antibody | 1:10–1:100 |
| CPRG (chlorophenylred-β-D-galactopyranoside) | 1 mg/mL |
| NaCl | 500 mM |
| K$_2$HPO$_4$ | 30 mM |
| EGTA | 10 mM |
| EDTA, Disodium | 0.6 mM |
| Na Azide | 20 mM |
| TWEEN-20 ® | 0.02% |
| pH | 6.80 |
| Acceptor reagent: | |
| Enzyme acceptor | 220 U/ml |
| Magnesium acetate | 5 mM |
| NaCl | 500 mM |
| K$_2$HPO$_4$ | 30 mM |
| EGTA | 10 mM |
| L-methionine | 10 mM |
| Na Azide | 20 mM |
| TWEEN-20 | 0.02% |
| pH | 6.80 |

® Registered TM of ICI Americas, Inc. for polyoxyethylene sorbitan

Figure 3:
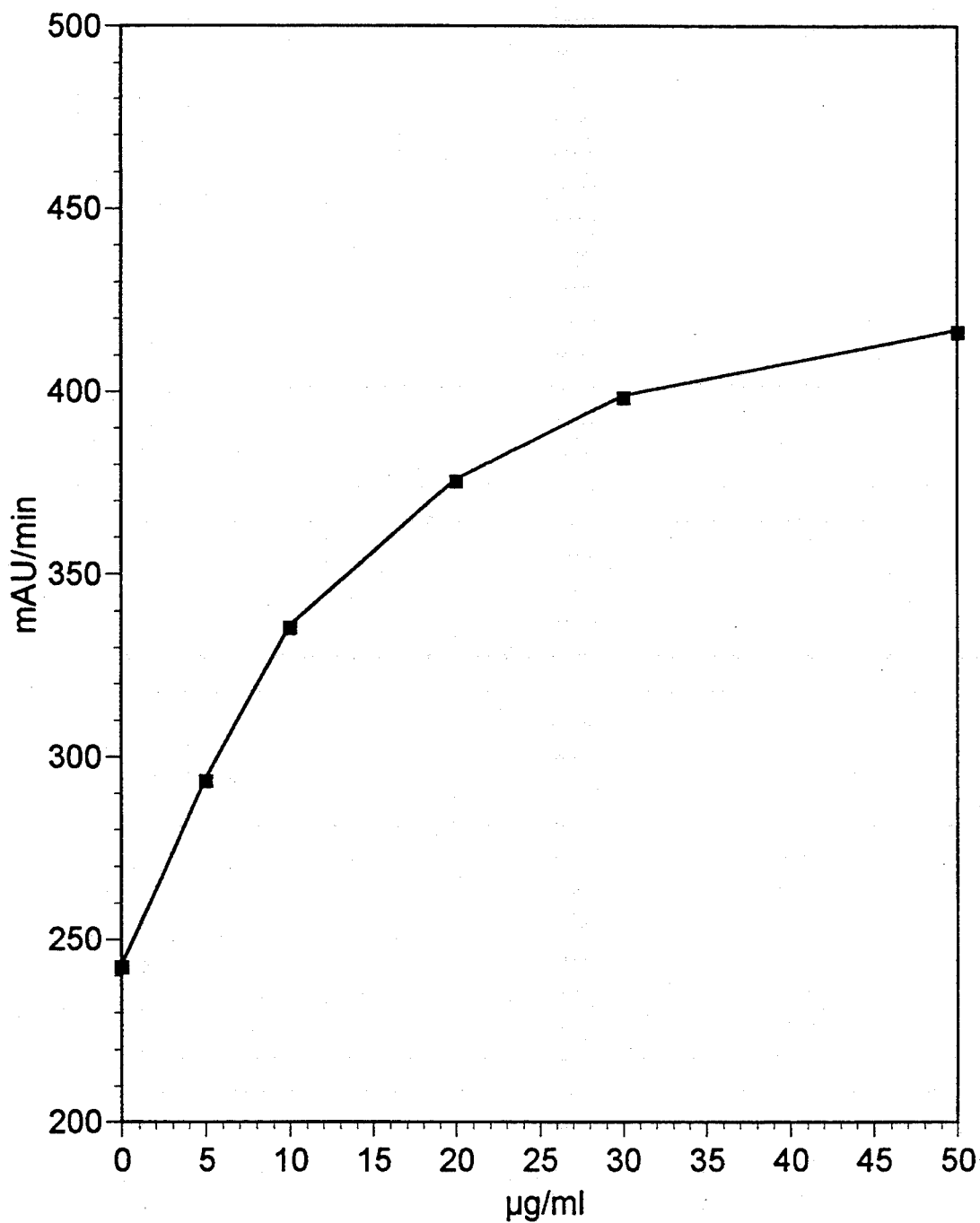
FIG. 3 is a graph showing a dose response curve at varying levels of procainamide using enzyme donor conjugates and antibodies of the present invention in a CEDIA assay.
Figure 4:
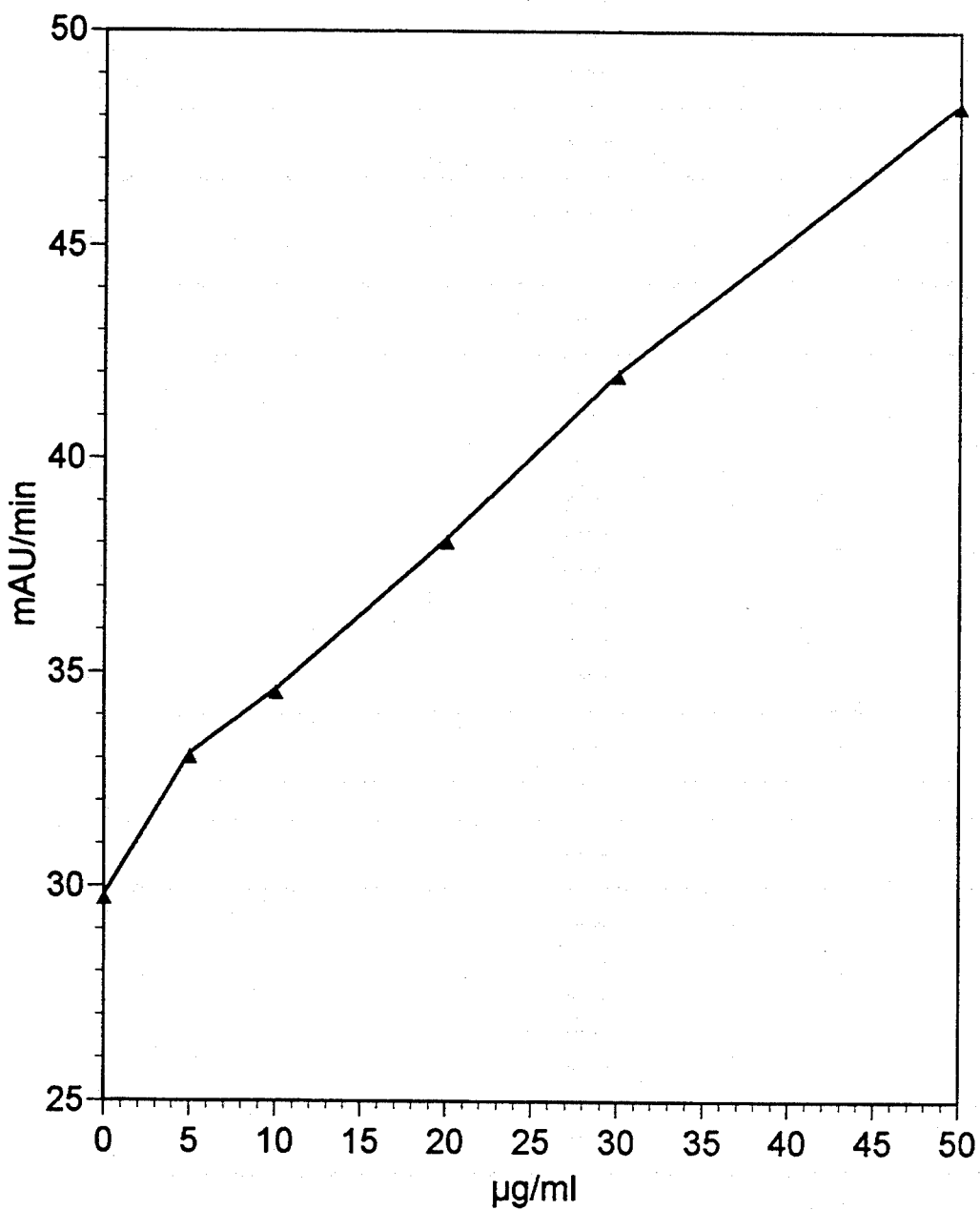
FIG. 4 is a graph showing a dose response curve at varying levels of NAPA using enzyme donor conjugates and antibodies of the present invention in a CEDIA assay.

Assays were performed using an HITACHI 717 autoanalyzer. The instrument dispensed 3 μl of sample containing NAPA or procainamide into a cuvette, and 200 μl of donor reagent was added. The mixture was allowed to incubate at 37° C. for 5 minutes, after which 150 μl of acceptor reagent was added. The absorbance rate was measured over the time period of 243.4 sec to 302.75 sec following the addition of the acceptor reagent. The primary wavelength used was 570 nm, with 660 nm used as the secondary wavelength. The absorbance rate at 570 nm was plotted against procainamide or NAPA concentration to construct a dose response curve. The curves obtained are shown in FIG. 3 and FIG. 4.

EXAMPLE 7

Cross-reactivity of NAPA and Procainamide Antibodies

The cross-reactivity for each of the clones was assayed as described in Example 6 using an HITACHI 717 autoanalyzer. Each clone was tested for cross-reactivity with the following analytes and concentrations: NAPA, 50 μg/ml; procainamide, 50 μg/ml; PADE, 50 μg/ml; NAPADE, 50 μg/ml; p-aminobenzoic acid (PABA), 50 μg/ml; and acetaminophen, 500 μg/ml. The percent cross-reactivity was calculated from the rate produced by each of the above analytes, and the apparent dose was found using FIGS. 3 and 4 as standard curves. The apparent dose of the analyte divided by the actual dose multiplied by 100 gives percent cross-reactivity.

Clone 13<PA>6 was checked for cross-reactivity with the above substances using the procedure in Example 6 and the standard curve in FIG. 3. The results found were as follows:

| Analyte | Rate (mAU/min) | Apparent Dose (μg/ml) | Actual Dose (μg/ml) | % Cross-reactivity |
|---|---|---|---|---|
| NAPADE | 242 | 0 | 50 | 0 |
| NAPA | 256 | 0.56 | 50 | 1.1 |
| PADE | 275 | 1.379 | 50 | 2.8 |
| PABA | 239 | 0 | 50 | 0 |
| Acetaminophen | 235 | 0 | 500 | 0 |

In another example, clone 24<NAPA>11.1 was also checked for cross-reactivity with these substances using the procedure in Example 6 and the standard curve in FIG. 4. The following results were found:

| Analyte | Rate (mAU/min) | Apparent Dose (μg/ml) | Actual Dose (μg/ml) | % Cross-reactivity |
|---|---|---|---|---|
| NAPADE | 30.1 | 2.58 | 50 | 5.2 |
| Procainamide | 29.4 | 0.56 | 50 | 0 |
| PADE | 30.3 | 2.74 | 50 | 5.5 |
| PABA | 29.2 | 0 | 50 | 0 |
| Acetaminophen | 29.2 | 0 | 500 | 0 |

It will be understood that the specification and examples are illustrative but not limitative of the present invention, and that other embodiments within the spirit and scope of the invention will suggest themselves to those skilled in the art.

What is claimed is:

1. A compound of the formula:

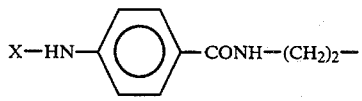

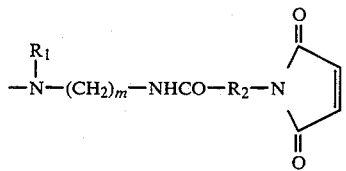

wherein:
X=hydrogen or acetyl;
$R_1$=an alkyl group having 1 to 3 carbon atoms;
m=an integer from 2 to 10; and
$R_2$=an alkyl, cycloalkyl or aryl group having 2 to 10 carbon atoms.

2. A compound of the formula:

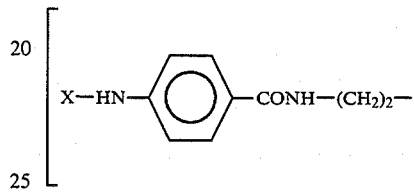

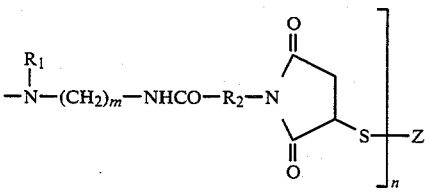

wherein:
X=hydrogen or acetyl;
$R_1$=an alkyl group having 1 to 3 carbon atoms;
m=an integer from 2 to 10;
$R_2$=an alkyl, cycloalkyl or aryl group having 2 to 10 carbon atoms;
Z=an immunogenic poly(amino acid), an enzyme donor polypeptide or a label selected from the group consisting of an enzyme, a substance having fluorescent properties and a radioactive substance; and
n=1 to p where p=MW of Z/1000.

3. The compound of claim 2, wherein Z is an immunogenic poly(amino acid).

4. The compound of claim 2, wherein Z is an enzyme donor polypeptide.

5. The compound of claim 2, wherein Z is keyhole limpet hemocyanin.

6. The compound of claim 2, wherein Z is an enzyme donor polypeptide of β-galactosidase.

7. The compound of claim 2, wherein $R_1$ is an alkyl group having 2 carbon atoms.

8. The compound of claim 2, wherein m is 2.

9. The compound of claim 2, wherein $R_2$ is $(CH_2)_2$.

10. An antibody to a compound according to claim 2 wherein Z is an immunogenic poly(amino acid) or polysaccharide.

11. An antibody to a compound according to claim 2 wherein X is hydrogen and Z is an immunogenic poly(amino acid).

12. An antibody to a compound according to claim 2 wherein X is acetyl and Z is an immunogenic poly(amino acid).

13. A monoclonal antibody to procainamide wherein said antibody has less than about 10 percent cross-reactivity with PADE.

14. A monoclonal antibody to NAPA wherein said antibody has less than about 10 percent cross-reactivity with NAPADE.

15. A method for determining procainamide in a sample comprising:
 (a) contacting said sample with
  (i) an enzyme donor polypeptide conjugate according to the compound of claim 2, wherein X is hydrogen and Z is an enzyme donor polypeptide of β-galactosidase;
  (ii) an enzyme acceptor polypeptide wherein said enzyme acceptor polypeptide is characterized by forming with said enzyme donor polypeptide conjugate an active enzyme complex having β-galactosidase activity in the absence of an antibody to procainamide;
  (iii) an antibody specific for procainamide, wherein said enzyme donor conjugate is capable of competitively binding to said antibody, thereby inhibiting the formation of active enzyme complex; and
  (iv) a substrate capable of reacting with said active enzyme complex, such that the rate of conversion of said substrate by said active enzyme complex can be monitored, and
 (b) measuring the rate of conversion of said substrate by said active enzyme complex as a measure of the amount of procainamide in said sample.

16. A method according to claim 15, wherein said antibody to procainamide is prepared in immunological response to a compound of the formula:

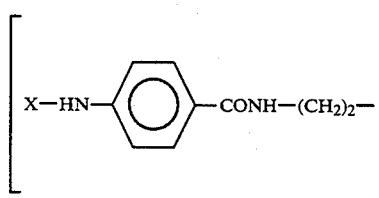

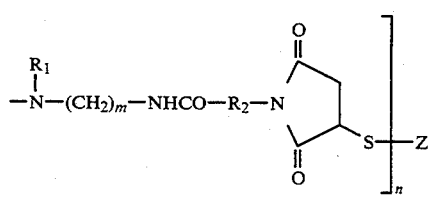

wherein:
X=hydrogen;
$R_1$=an alkyl group having 1 to 3 carbon atoms;
m=an integer from 2 to 10;
$R_2$=an alkyl, cycloalkyl or aryl group having 2 to 10 carbon atoms;
Z=an antigenic poly(amino acid); and
n=1 to p where p=MW of Z/1000.

17. A method for determining NAPA in a sample comprising:
 (a) contacting said sample with
  (i) an enzyme donor polypeptide conjugate according to claim 2, wherein X is acetyl and Z is an enzyme donor polypeptide of β-galactosidase;
  (ii) an enzyme acceptor polypeptide wherein said enzyme acceptor polypeptide is characterized by forming with said enzyme donor polypeptide conjugate an active enzyme complex having β-galactosidase activity in the absence of an antibody to NAPA;
  (iii) an antibody specific for NAPA, wherein said enzyme donor conjugate is capable of competitively binding to said antibody, thereby inhibiting the formation of active enzyme complex; and
  (iv) a substrate capable of reacting with said active enzyme complex, such that the rate of conversion of said substrate by said active enzyme complex can be monitored, and
 (b) measuring the rate of conversion of said substrate by said active enzyme complex as a measure of the amount of NAPA in said sample.

18. A method according to claim 17, wherein said antibody to NAPA is prepared in immunological response to a compound of the formula:

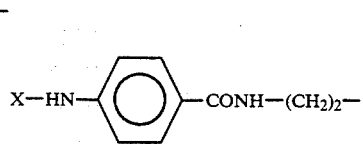

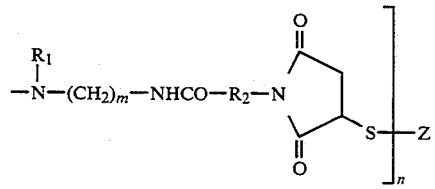

wherein:
X=acetyl;
$R_1$=an alkyl group having 1 to 3 carbon atoms;
m=an integer from 2 to 10;
$R_2$=an alkyl, cycloalkyl or aryl group having 2 to 10 carbon atoms;
Z=an antigenic poly(amino acid) or polysaccharide; and
n=1 to p where p=MW of Z/1000.

* * * * *